US007181283B2

(12) United States Patent
Hettrick et al.

(10) Patent No.: US 7,181,283 B2
(45) Date of Patent: Feb. 20, 2007

(54) SYSTEM AND METHOD FOR CONTROLLING IMPLANTABLE MEDICAL DEVICE PARAMETERS IN RESPONSE TO ATRIAL PRESSURE ATTRIBUTES

(75) Inventors: Douglas A. Hettrick, Blaine, MN (US); Todd M. Zielinski, Minneapolis, MN (US); Amber L Jaeger, West Bend, WI (US); Nicole M. Campbell, Milwaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 78 days.

(21) Appl. No.: 11/097,408

(22) Filed: Mar. 31, 2005

(65) Prior Publication Data

US 2006/0224204 A1 Oct. 5, 2006

(51) Int. Cl.
*A61N 1/365* (2006.01)
*A61B 5/021* (2006.01)
(52) U.S. Cl. .......................... 607/23; 607/18; 607/17; 600/485; 600/486
(58) Field of Classification Search .................. 607/17, 607/18, 23, 9; 600/485, 486, 508, 481
See application file for complete search history.

(56) References Cited

U.S. PATENT DOCUMENTS

| 4,899,752 | A | * | 2/1990 | Cohen | 607/23 |
| 5,129,394 | A | * | 7/1992 | Mehra | 607/23 |
| 5,743,267 | A | * | 4/1998 | Nikolic et al. | 600/485 |
| 6,328,699 | B1 | * | 12/2001 | Eigler et al. | 600/486 |
| 2003/0199933 | A1 | * | 10/2003 | Struble | 607/17 |
| 2004/0147969 | A1 | * | 7/2004 | Mann et al. | 607/17 |
| 2004/0167580 | A1 | * | 8/2004 | Mann et al. | 607/17 |
| 2004/0172077 | A1 | * | 9/2004 | Chinchoy | 607/17 |
| 2004/0215266 | A1 | * | 10/2004 | Struble et al. | 607/17 |
| 2006/0064135 | A1 | * | 3/2006 | Brockway | 607/17 |
| 2006/0079793 | A1 | * | 4/2006 | Mann et al. | 600/486 |
| 2006/0137457 | A1 | * | 6/2006 | Zdeblick | 607/18 |

* cited by examiner

*Primary Examiner*—Robert Pezzuto
*Assistant Examiner*—Eugene Wu
(74) *Attorney, Agent, or Firm*—Girma Wolde-Michael; Daniel G. Chapik

(57) ABSTRACT

In an implantable medical device a real-time left atrial pressure ("LAP") signal obtained from a patient's heart is used as a feedback control mechanism to adjust one or more device parameters. In one example the device identifies specific characteristics and attributes of the LAP signal that correlate to hemodynamic performance, and adjusts the device parameters to optimize the LAP characteristics and attributes. In a dual-chamber pacing system, the controlled operating parameter may include the atrioventricular pacing delay, and LAP attribute suitable for controlling the atrioventricular pacing delay time intervals of v-wave, a-wave, and/or c-wave characteristics of the LAP signal.

17 Claims, 9 Drawing Sheets

SYSTEM AND METHOD FOR CONTROLLING IMPLANTABLE MEDICAL DEVICE PARAMETERS IN RESPONSE TO ATRIAL PRESSURE ATTRIBUTES

TECHNICAL FIELD

The present invention relates generally to medical devices. More particularly, the present invention relates to devices and techniques for controlling therapy signal parameters of an implantable medical device.

BACKGROUND

The heart is responsible for circulating blood throughout the body. The heart includes four chambers: the left atrium ("LA"); the right atrium ("RA"); the left ventricle ("LV"); and the right ventricle ("RV"). Blood that has circulated through the body enters the RA, flows into the RV, and out of the heart to the lungs. Oxygenated blood from the lungs enters the LA, flows into the LV, and out of the heart to the various organs of the body. A normal heart rhythm is associated with electrical and mechanical activity corresponding to the atrial and ventricular contractions. A normal cardiac cycle includes systole (contraction of the ventricles causing blood to move through the body) and diastole (relaxation of the ventricles during which the ventricles fill with blood). Thus, when a ventricle fills, the corresponding atrium empties its contents into the ventricle.

A normal heart rhythm results in an efficient pumping of blood throughout the body. In this regard, the atrioventricular contractions must be properly timed to enable the transfer of blood between the chambers of the heart. Normal hearts generate the electrical signals necessary to regulate the atrioventricular timing and heartbeat. A number of disorders, however, can adversely impact the operation of the heart. Medical devices, such as pacing systems, provide electrical stimuli to the heart in an attempt to correct an abnormal rhythm and/or to maintain a normal rhythm.

The prior art includes many different types of implantable medical devices ("IMDs"), such as pacing systems, cardiac resynchronization therapy devices, defibrillators, and the like. A given IMD may have a number of adjustable electrical and/or mechanical parameters associated with diagnostic or therapeutic functions, and such adjustable parameters may be regulated by the IMD using suitable control techniques. For example, a dual-chamber pacing device typically controls the atrioventricular ("AV") delay in a manner that strives to optimize cardiac performance. Known adjustment techniques often rely upon empirical or historical data, or are based upon the heart rate or activity level of the patient. Another known technique uses an open loop feedback system having a separate device (typically an external device) that obtains and processes physiologic data from the patient. The physiologic data is analyzed by the separate device, and the IMD is reprogrammed if necessary. Such open loop systems, however, can be cumbersome, inconvenient, and expensive to use.

Accordingly, it is desirable to have technique for controlling IMD parameters in a closed loop manner. Furthermore, other desirable features and characteristics of the present invention will become apparent from the subsequent detailed description and the appended claims, taken in conjunction with the accompanying drawings and the foregoing technical field and background.

BRIEF SUMMARY

Systems and methods disclosed herein adjust IMD operating parameters in response to a left atrial pressure ("LAP") signal that is directly measured. In one example embodiment, an IMD receives a LAP signal from an implanted LAP sensor, and the IMD processes the LAP signal to identify certain characteristics, attributes, and/or signal morphologies that correlate to cardiac performance of the patient. The use of a real-time LAP signal by the IMD creates a closed loop system that need not rely upon any external or separate devices. In addition, the LAP signal facilitates optimization of the IMD parameters according to measured rhythmic mechanical responses of the heart.

The above and other aspects of the invention may be carried out in one form by a method for controlling implantable medical device parameters. The method involves: obtaining a LAP signal; identifying at least one attribute of the LAP signal; and automatically adjusting at least one output parameter of an IMD in response to the at least one attribute.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely illustrative only and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of medical devices and therapies and that the system described herein is merely one exemplary application for the invention.

For the sake of brevity, conventional techniques related to IMD sensor signal processing, LAP sensing, the adjustment and control of IMD therapy signals, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 7:
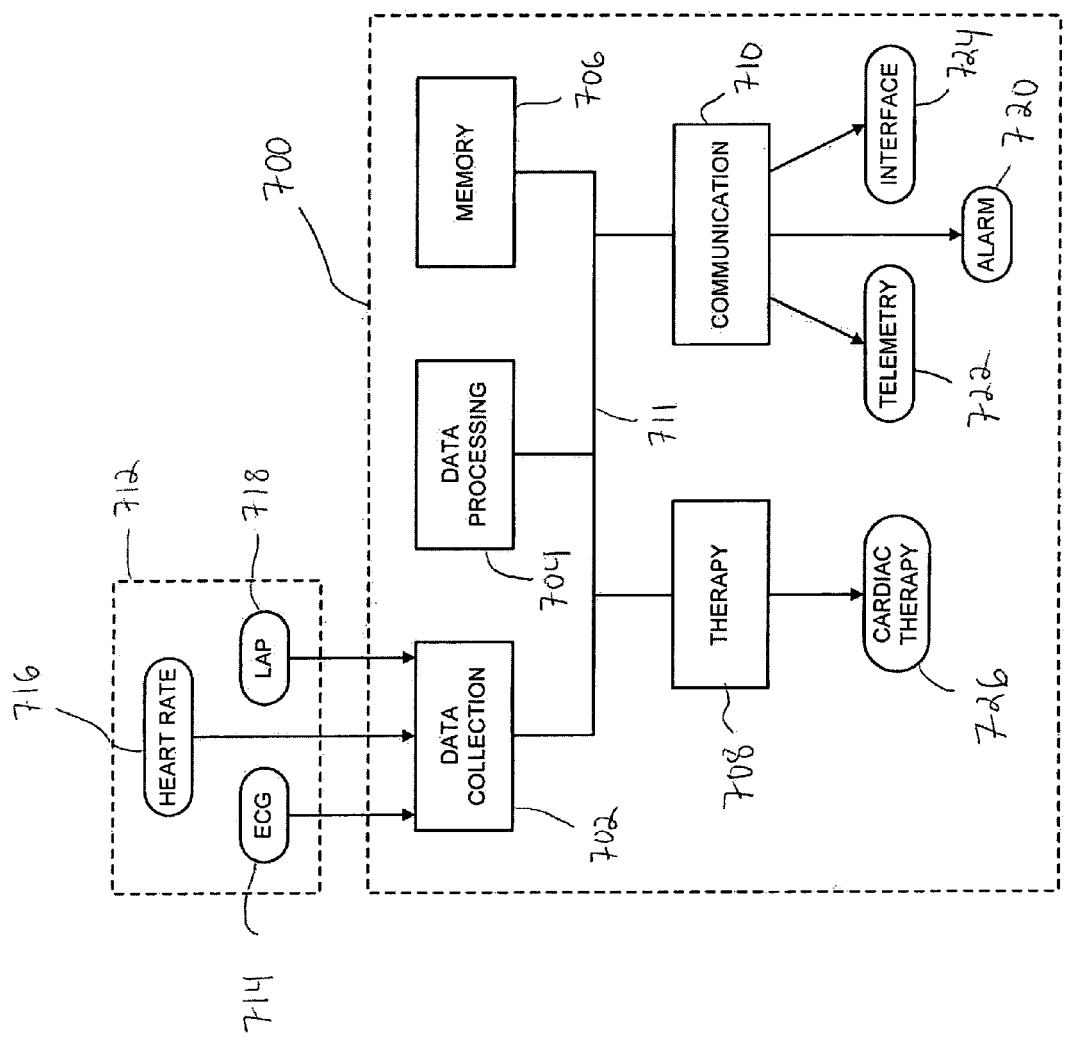
FIG. 7 is a schematic representation of a portion of an IMD configured in accordance with an example embodiment of the invention.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically. Thus, although the schematic shown in FIG. 7 depicts one example arrangement of processing elements, additional intervening elements, devices, features, or components may be present in an actual embodiment (assuming that the functionality of the system is not adversely affected).

In connection with the operation of an IMD, implantable sensors may be expected to provide diagnostic data to the IMD and/or to facilitate automated feedback control of the IMD. For example, direct measurement of LAP may be well suited to monitor ventricular preload and hence pulmonary congestion, diagnose atrial arrhythmias, and to discriminate atrial fibrillation from atrial flutter. It would also be useful, however, if the same implantable LAP sensor could be used to optimize device timing. In this regard, an example embodiment of the invention incorporates real-time LAP signals for use as feedback control (preferably closed loop, but also applicable to open loop) of IMD settings or operational parameters. Specifically, inappropriate AV delay timing, whether too short or too long, may result in mitral valve regurgitation or other suboptimal heart rhythm conditions leading to suboptimal cardiac output. The techniques described in more detail below may be utilized to optimize AV timing, and therefore reduce the likelihood of mitral valve regurgitation, by monitoring the quantitative features and attributes of a real-time LAP signal. Furthermore, the techniques described herein may be utilized to diagnose mitral valve regurgitation and other heart rhythm conditions.

Figure 1:
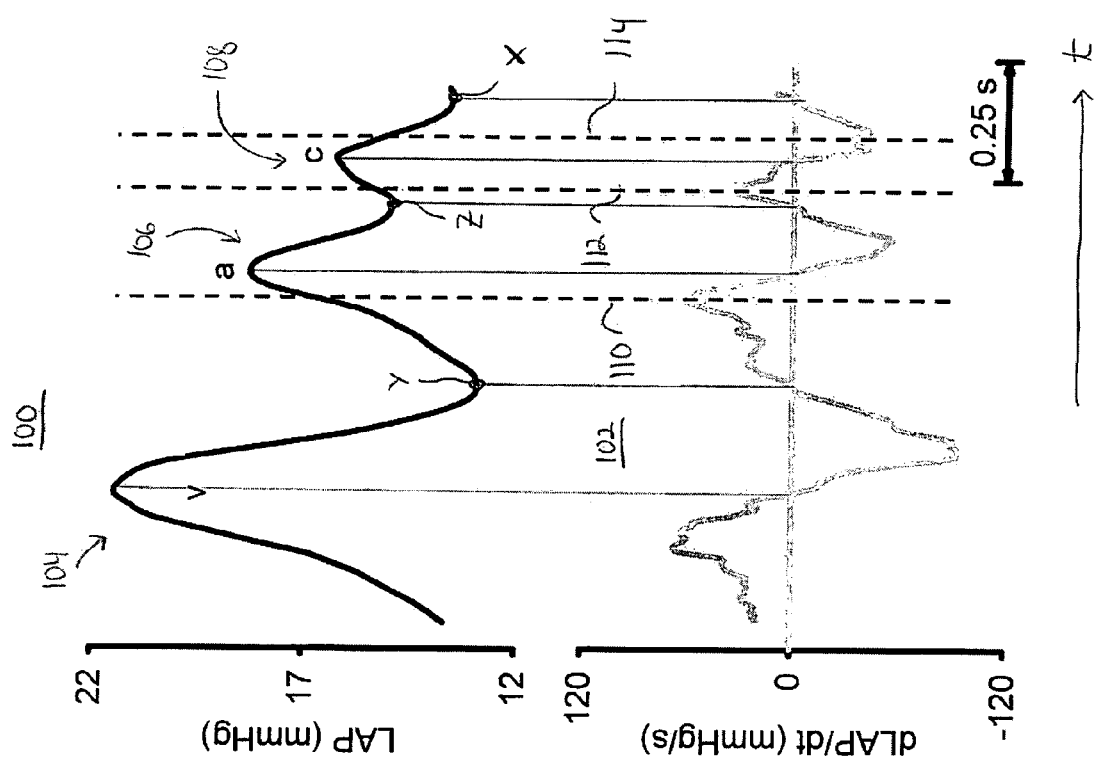
FIG. 1 is a diagram showing an example graph of a LAP signal along with an example graph of the first derivative of the LAP signal.

FIG. 1 is a diagram showing an example graph of a LAP signal 100 along with an example graph of a secondary signal 102 that represents the first derivative of the LAP signal (i.e., the dLAP/dt signal). It should be appreciated that these graphs are merely examples and that the actual LAP characteristics will vary from patient to patient, vary according to the current patient condition, and vary over time. Referring to LAP signal 100, during normal sinus rhythm, left atrial pressure is described by classical features of LAP signal 100 including a v-wave characteristic 104 corresponding to mitral valve opening, an a-wave characteristic 106 corresponding to atrial contraction, and a c-wave characteristic 108 corresponding to isovolumic contraction and sequential opening of the aortic valve. The corresponding left atrium volume decreases following mitral valve opening and again at atrial contraction as it empties its contents into the left ventricle.

Additional attributes and features of LAP signal 100 are identified in FIG. 1. For example, the "z" point is the local minimum following the atrial contraction and closure of the mitral valve immediately preceding ventricular systole. The negative x-wave characteristic (or "x descent" or systolic collapse) is associated with the descent of the mitral ring during ventricular ejection. The "y descent" (or "diastolic collapse") following mitral valve opening is associated with early ventricular filling and passive atrial emptying.

Figure 2:
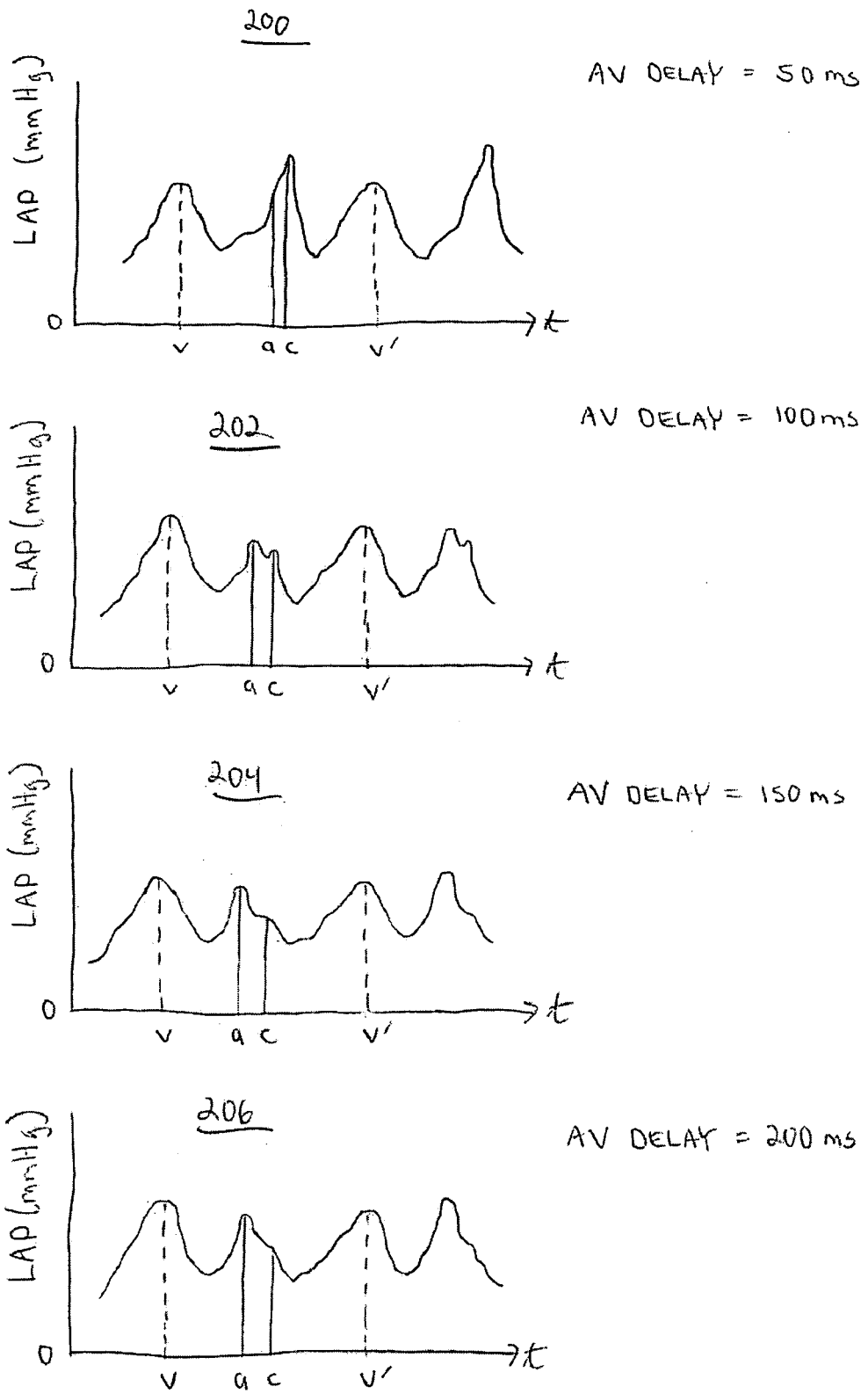
FIG. 2 is a series of graphs of a LAP signal for different AV delay settings.

The salient features of a LAP signal are also shown in FIG. 2, which depicts a series of example LAP signal graphs corresponding to different AV delay settings for a dual-chamber pacing device. A first LAP signal 200 corresponds to an AV delay of 50 ms; a second LAP signal 202 corresponds to an AV delay of 100 ms; a third LAP signal 204 corresponds to an AV delay of 150 ms; and a fourth LAP signal 206 corresponds to an AV delay of 200 ms. The various v-wave, a-wave, and c-wave characteristics for each graph are identified on the respective time axis (in FIG. 2, the "v prime" identifier represents the next v-wave in the ongoing cardiac cycle). FIG. 2 graphically illustrates the different timing intervals between the v-wave, a-wave, and c-wave characteristics for each AV delay setting. Notably, the amplitude of the c-wave and the time period between the a-wave and the c-wave are associated with AV delay. Generally, the amplitude of the c-wave peak decreases with increasing AV delay, and the time period between the a-wave and c-wave peaks increases with increasing AV delay. As described in more detail below, the amplitude of the c-wave characteristic and/or a temporal indicator based upon the a-wave and c-wave characteristics may be used for AV delay optimization.

The c-v interval ($t_{cv}$) corresponds to left ventricular ejection and is independent of AV delay and somewhat independent of heart rate. Thus, the v-c interval ($t_{vc}$) is primarily determined by heart rate. Furthermore, the AV delay interval determines the a-c interval ($t_{ac}$). Thus, the ratio of $t_{va}$ to $t_{vc}$ depends on both heart rate and the AV delay. As described in more detail below, this ratio may be used for AV delay optimization. Generally, as indicated by the graphs in FIG. 2, LAP data can be used to optimize LV function, depending on the heart rate.

Figure 3:
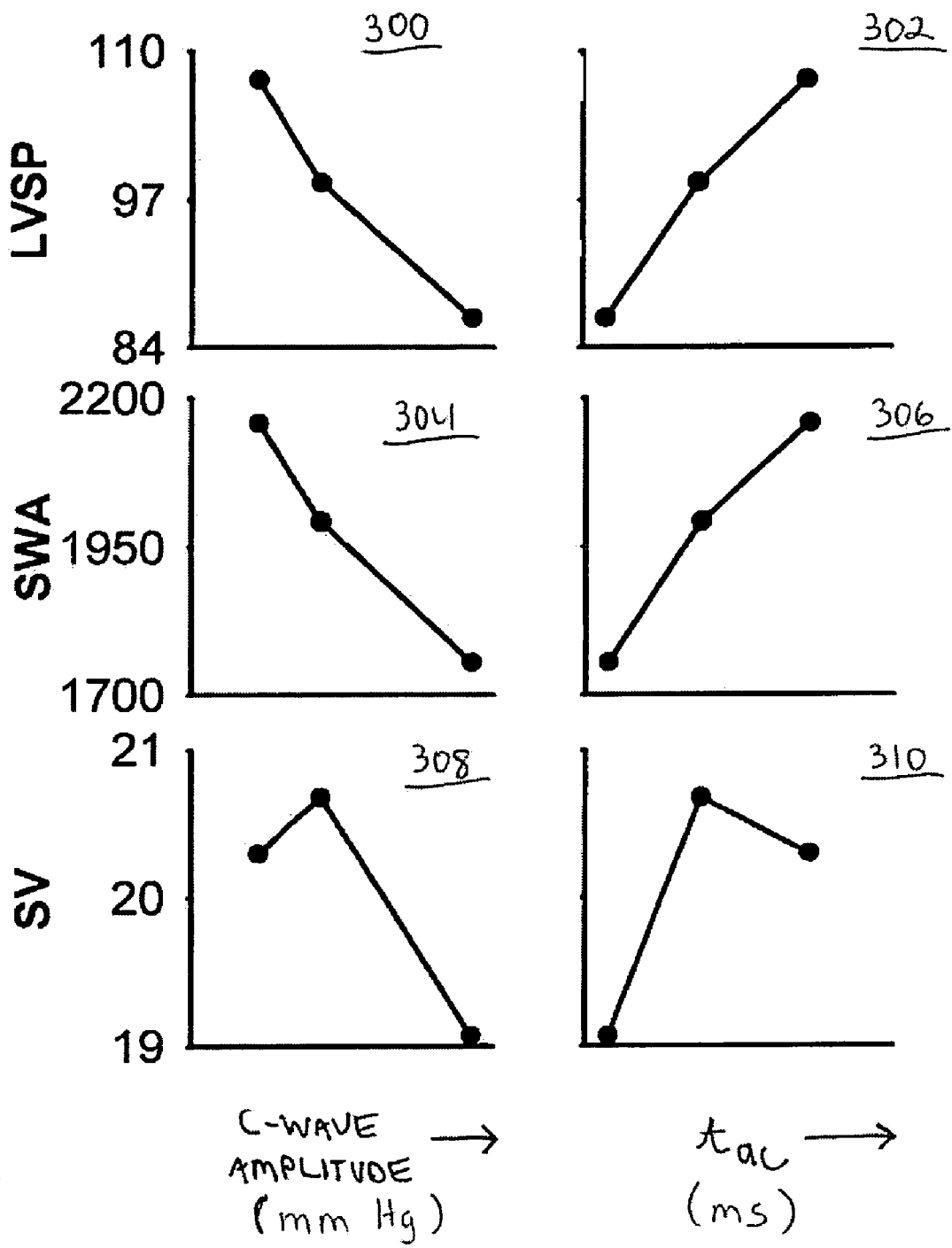
FIG. 3 is number of graphs depicting the quantitative correlation between LAP signal characteristics and various indices of LV performance.

FIG. 3 includes a number of graphs that depict the quantitative correlation between c-wave amplitude and $t_{ac}$ with various accepted indices of LV performance, namely, LV systolic pressure ("LVSP"), stroke work area ("SWA"), and stroke volume ("SV"). Generally, higher values of LVSP, SWA, and SV correspond to better LV performance. As shown in graphs 300 and 302, the LVSP increases with decreasing c-wave amplitude and with increasing $t_{ac}$. As shown in graphs 304 and 306, the SWA also increases with decreasing c-wave amplitude and with increasing $t_{ac}$. Finally, as shown in graphs 308 and 310, the SV generally increases with decreasing c-wave amplitude and with increasing $t_{ac}$. This data further indicates that LAP data can be used to optimize LV function, depending on the heart rate.

Figure 4:
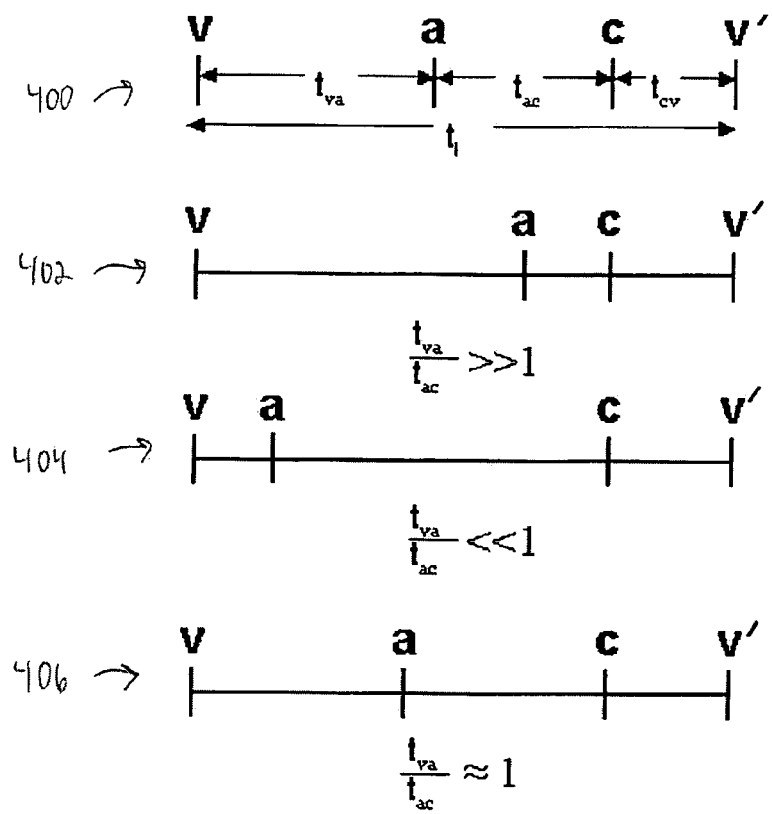
FIG. 4 is a diagram showing various timing relationships of LAP signal attributes.

FIG. 4 is a diagram showing various timing relationships of LAP signal attributes. More specifically, FIG. 4 conceptually illustrates how $t_{va}$ and $t_{ac}$, but not $t_{cv}$, vary with AV delay. The first timing diagram 400 generally depicts one cardiac cycle (between the two v-wave points) and the various timing intervals between the v-wave, a-wave, and c-wave characteristics. The second timing diagram 402 schematically depicts an exaggerated state where the ratio of $t_{va}$ to $t_{ac}$ is much greater than a desired target ratio. Although the target ratio is approximately one in this example, it may be any suitable value depending upon the particular application, device, current heart rate, patient, and/or medical condition of the patient. The third timing diagram 404 schematically depicts an exaggerated state where the ratio of $t_{va}$ to $t_{ac}$ is much less than the target ratio of one. In practice, the conditions depicted in timing diagram 402 and timing diagram 404 are less than optimal. In contrast, the fourth timing diagram 406 schematically depicts a desirable state where the ratio of $t_{va}$ to $t_{ac}$ is approximately equal to the desired target ratio of one. Thus, $t_{ac}$ or a ratio of $t_{va}$ and $t_{ac}$ can be used as a feedback variable to control the AV delay or other device operations of an IMD.

Figure 5:
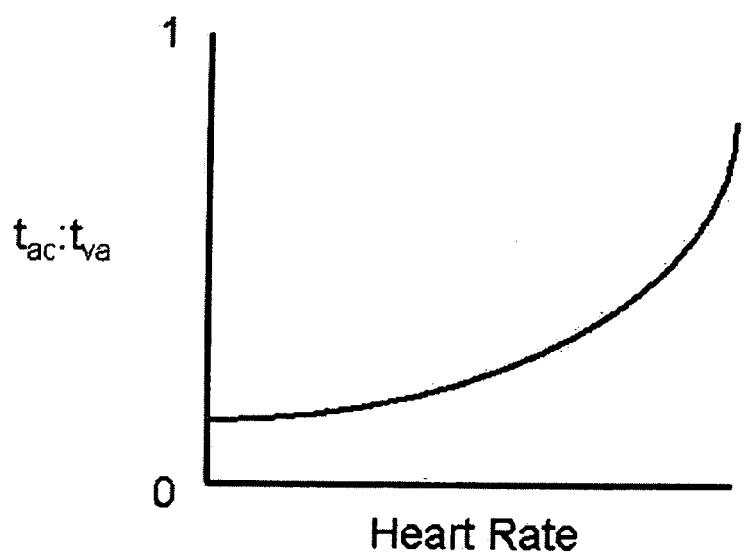
FIG. 5 is a graph depicting an example relationship between a target ratio of LAP signal attributes versus heart rate.

FIG. 5 is a graph depicting an example relationship between a target $t_{ac}:t_{va}$ ratio versus heart rate. This graph shows conceptually how a ratio of $t_{ac}$ and $t_{va}$ can be used to adjust or optimize AV delay. For example, if the heart rate is relatively low (e.g., 60 bpm), the desired target $t_{ac}:t_{va}$ ratio may be about 0.3. If, however, the heart rate is relatively high (e.g., 120 bpm), the desired target $t_{ac}:t_{va}$ ratio may be about 0.8. Accordingly, a curve relating the desired target ratio to heart rate could be generated. This relationship may be linear or non-linear and may have any desirable attributes. Indeed, the graph shown in FIG. 5 is merely one possible non-limiting example. In a practical IMD embodiment, the relationship depicted in FIG. 5 may be realized as a suitable algorithm or program configured to adjust AV delay based upon heart rate and LAP signal attributes.

In another embodiment, the amplitude of the c-wave characteristic could be used, independent of heart rate, to adjust AV delay and/or other device parameters. Any number of additional algorithms could be derived based on these basic principles. For example the LAP signal could be integrated to obtain the area beneath the c-wave section, and that area could be used in lieu of the c-wave amplitude.

In yet another embodiment, correlated with the amplitude of the c-wave or distortion of the c-wave morphology during LV isovolumetric contraction, the slope of the LAP signal between the a-wave peak and the c-wave peak (or distortion in that LAP signal segment), the slope of the LAP signal between the c-wave peak and the x-wave valley (or distortion in that LAP signal segment), and/or the slope of the LAP signal between the x-wave valley and the v-wave peak (or distortion of that LAP signal segment) could be used as an indicator of the magnitude of mitral valve regurgitation since the mitral valve closes just after the a-wave peak pressure amplitude and opens just after the v-wave peak pressure amplitude. Consequently, analyzing the slopes of various LAP signal segments may be of clinical diagnostic value and may be utilized to adjust or optimize AV delay and other device parameters.

Moreover, the slope of the c-x segment of the LAP signal, which corresponds to the initial phase of rapid LV ejection, and the slope of the x-v segment of the LAP signal, which corresponds to the second phase of rapid LV ejection and the final reduced phase of LV ejection, could be used as additional indicators for detecting early onset cardiomyopathies that lead to LV dysfunction and AV and VV mechanical asynchrony.

From the above discussion, it follows that characteristics and attributes of the LAP signal and/or characteristics and attributes of a derivative of the LAP signal (see graph 102 of FIG. 1) may be utilized to adjust IMD parameters such as AV delay. In addition to AV delay, however, a LAP signal could be used to evaluate additional aspects of cardiac performance. For example, a suitable algorithm could be used to optimize the amplitude of the x-wave valley or, more simply, to track the amplitude of the x-wave valley. Since the x-wave is associated with LV systole, changes in x-wave morphology or amplitude could be correlated with changes in systolic left ventricular function. Many other similar algorithms could be conceived using the morphology of the LAP signal and/or the morphology of a signal based upon the LAP signal (e.g., a derivative of the LAP signal, an integral of the LAP signal, etc.) to evaluate or optimize atrial and ventricular performance.

Figure 6:
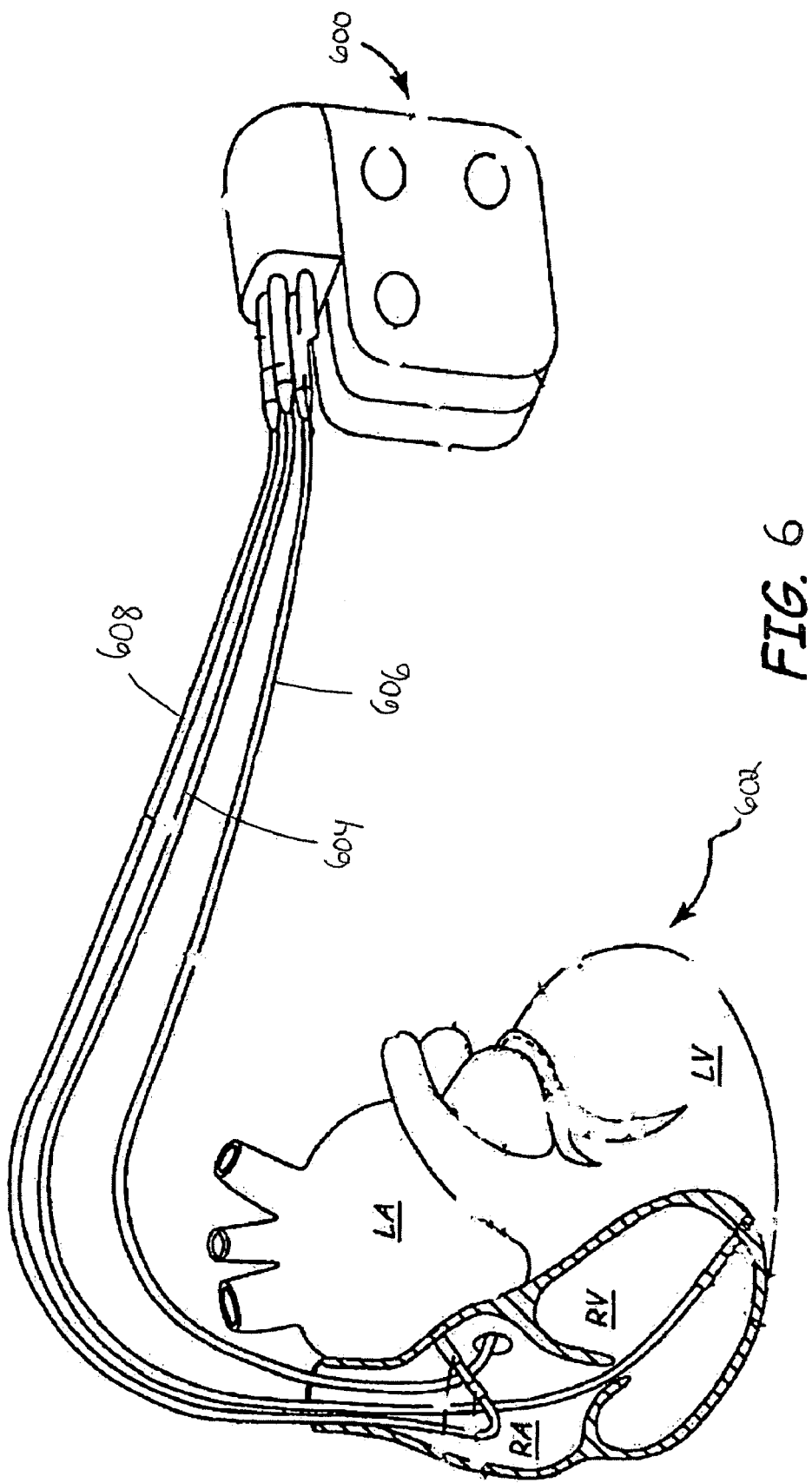
FIG. 6 is a diagram showing an IMD in conjunction with a patient's heart.

FIG. 6 is a diagram showing an IMD 600 in conjunction with a patient's heart 602. In this example, IMD 600 is connected to heart 602 to support both monitoring and therapy features, as will be described below. In practical embodiments, IMD 600 can be any device that supports dual-chamber pacing. In this regard, IMD 600 may include or be configured as a pacing system, a defibrillator system, a cardiac resynchronization therapy device, or the like. IMD 600 suitably collects and processes data about heart 602 from one or more sources (e.g., LAP sensor, heart rate monitor, blood pressure monitor, electrocardiogram ("ECG") waveform, electrogram waveform ("EGM"), or the like). IMD 600 may further provide therapy or other response to the patient as appropriate, and as described more fully below. As shown in FIG. 6, IMD 600 may be generally flat and thin to permit subcutaneous implantation within a human body, e.g., within upper thoracic regions or the lower abdominal region. IMD 600 may include a hermetically-sealed housing that encloses a processor, a digital memory, and other components as appropriate to produce the desired functionalities of the device.

The processor of IMD 600 (not shown in FIG. 6) may be implemented with any type of microprocessor, digital signal processor, application specific integrated circuit ("ASIC"), field programmable gate array ("FPGA") or other integrated or discrete logic circuitry programmed or otherwise configured to provide functionality as described herein. The processor executes instructions stored in the digital memory to provide functionality as described below. Instructions provided to the processor may be executed in any manner, using any data structures, architecture, programming language and/or other techniques. The digital memory of IMD 600 (not shown in FIG. 6) is any storage medium capable of maintaining digital data and instructions provided to the processor such as a static or dynamic random access memory ("RAM"), or any other electronic, magnetic, optical or other storage medium.

As further shown in FIG. 6, IMD 600 may receive one or more cardiac leads for connection to circuitry enclosed within the housing. In the example of FIG. 6, IMD 600 receives a right ventricular endocardial lead 604, a left atrial septal lead 606, and a right atrial endocardial lead 608, although the particular cardiac leads used will vary widely from embodiment to embodiment. In addition, the housing of IMD 600 may function as an electrode, along with other electrodes that may be provided at various locations on the housing of IMD 600. IMD 600 preferably includes a LAP lead (for example, lead 606 may be a LAP lead) that provides a real-time LAP signal to IMD 600 from the LA of heart 602. The LAP sensor may be contained on an independent lead, or may be integrated into a pacing or defibrillation lead. In alternate embodiments, other data inputs, leads, electrodes and the like may be provided. Ventricular lead 604 may include, for example, pacing electrodes and defibrillation coil electrodes (not shown) for purposes of pacing, cardioversion, and/or defibrillation.

In operation, IMD 600 suitably obtains data about heart 602 via leads 604/606/608 and/or other sources. This data is provided to the internal processor, which suitably analyzes the data and provides a response as appropriate. In particular, IMD 600 generates one or more therapy signals that are preferably optimized in accordance with the obtained data. In the example embodiment, IMD 600 selects or adjusts an electrical stimulation therapy and coordinates the delivery of the therapy by IMD 600 or another appropriate device. Optional therapies that may be applied in various embodiments may include drug delivery, neurostimulation, modifications in pacing rate, and/or the like.

FIG. 7 is a schematic representation of a portion of an IMD configured in accordance with an example embodiment of the invention. In particular, FIG. 7 depicts an exemplary data processing layout for an IMD processor architecture 700, which may be located within the housing of a suitable IMD as described herein. In this example, processor architecture 700 includes at least a data collection module 702, a data processing module 704, a suitable amount of memory 706, a therapy module 708, and/or a communication module 710. These modules may be coupled to each other via a suitable data communication bus or arrangement 711. Each of the various modules may be implemented with computer-executable instructions stored in memory 706 and executing on processor architecture 700, or in any other practical manner. The exemplary modules and blocks shown in FIG. 7 are intended to illustrate one logical model for implementing an IMD in accordance with the invention, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

In accordance with the practices of persons skilled in the art of computer programming, the invention may be described herein with reference to symbolic representations of operations that may be performed by the various computing components, modules, or devices. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the IMDs described herein are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a hard disk, a fiber optic medium, or the like. The computer data signal may include any signal that can propagate over a transmission medium such as electronic network channels, optical fibers, air, electromagnetic paths, or RF links.

Data collection module 702 suitably interacts with one or more data sources 712 to obtain data about the patient. Data sources 712 include any source of information about the patient's heart, and possibly other physiologic information. In various embodiments, data sources 712 may include an ECG source 714 that provides electrical impulses or other observed signals that can be used to model the patient's ECG waveform. Other data sources 712 may include a heart rate sensor 716 and a LAP sensor or monitor 718. In practice, an IMD may also utilize an accelerometer, a sensor for determining cardiac conduction time, temperature sensors, blood pH sensors, and/or other known data sources. The various data sources 712 may be provided alone or in any combination with each other, and may vary widely from embodiment to embodiment.

LAP sensor 718 is suitably configured to measure the real-time LAP of the patient's heart and to provide raw LAP data to data collection module 702. In turn, data collection module 702 and/or data processing module 704 can convert the raw LAP data into a usable LAP signal for analysis as described herein. A practical IMD can utilize any suitable LAP sensor 718, including, without limitation: LAP sensors that are mounted through the atrial septal wall of the heart; LAP sensors that utilize structures of the heart as a transducer membrane, such as the right atrial fossa ovalis; and LAP sensors that are inserted through the left atrial appendage or anterior posterior or lateral appendage, or through the mitral valve or via the pulmonary veins. Indeed, processor architecture 700 can be configured to accommodate the specific LAP signal format and characteristics associated with the particular LAP sensor or sensors deployed with the IMD.

Data collection module 702 suitably receives data from each of the data sources 712 by polling each of the data sources 712, by responding to interrupts or other signals generated by the data sources 712, by receiving data at regular time intervals, or according to any other temporal scheme. In particular, data collection module 702 is configured to obtain a LAP signal from the patient for processing. Data may be received at data collection module 702 in digital or analog format according to any protocol. If any of the data sources 712 generate analog data, data collection module 702 suitably translates the analog signals to digital equivalents using any form of analog-to-digital conversion scheme presently known or subsequently developed. Data collection module 702 may also convert data from protocols used by data sources 712 to data formats acceptable to data processing module 704, as appropriate. It should be appreciated that LAP sensor 718, processor architecture 700, data collection module 702, and any corresponding logical elements, individually or in combination, are example means for obtaining a LAP signal of a patient as used herein.

Data processing module 704 is any circuit, programming routine, application or other hardware/software module that is capable of processing data received from data collection module 702. In various embodiments, data processing module 704 is a software application executing on processor architecture 700 to implement the processes described below. Accordingly, data processing module 704 interprets received LAP signals, generates or analyzes signals based upon or derived from received LAP signals, and/or handles other data to adjust one or more operating parameters of the IMD.

In an exemplary embodiment, data processing module 704 receives LAP signal data and/or other appropriate information from data collection module 702 and interprets the data using conventional digital signal processing techniques. For example, data processing module 704 may generate a secondary signal that is based upon the first derivative of the LAP signal (such a secondary signal may be referred to herein as a dLAP/dt signal as depicted in FIG. 1). In this regard, data processing module 704, processor architecture 700, and any corresponding logical elements, individually or in combination, are example means for generating secondary signals based upon the LAP signal.

As described in more detail below, data processing module 704 is configured to identify at least one attribute of the LAP signal, and/or at least one attribute of a secondary signal based upon the LAP signal, and correlate the identified attributes to a hemodynamic status or cardiac performance of the patient. In this manner, the LAP signal data can be utilized as a feedback control mechanism to adjust the therapy delivered by the IMD. It should be appreciated that data processing module 704, processor architecture 700, and any corresponding logical elements, individually or in combination, are example means for identifying attributes of the LAP signal and/or the dLAP/dt signal.

Communication module 710 is any circuit or routine that facilitates the transfer of data, information, reports, or programming instructions between the IMD and an external device, system, or person (e.g., the patient, a physician, or a caregiver). In various embodiments, communication module may be configured to generate an audible or visible alarm 720, handle wireless messages via a telemetry circuit 722, or manage the transmission of other data using any suitable interface 724. In this regard, communication module 710 may facilitate open loop feedback control of the IMD operating parameters by transmitting LAP signals or LAP signal attributes to an external processing system that responds with programming instructions to adjust the AV delay or other IMD parameters in the manner described herein.

Therapy module 708 is any circuit, software application or other component that is configured to deliver cardiac therapy 726 to the patient. In the example embodiment, therapy module 708 is configured to provides dual-chamber pacing therapy as one form of cardiac therapy 726. In some embodiments, therapy module 708 may be alternatively or additionally configured to deliver other modes of pacing, post-extrasystolic potentiation, cardioversion, defibrillation and/or any other therapy. In the example embodiment, therapy module 708 is configured to automatically adjust at least one hemodynamic parameter of a therapy signal in response to one or more attributes of the LAP signal and/or in response to one or more attributes of a secondary signal that is based upon the LAP signal. The hemodynamic parameter may, for example, be the AV delay associated with a dual-chamber pacing mechanism. It should be appreciated that therapy module 708, cardiac therapy 726, processor architecture 700, and any corresponding logical elements, individually or in combination, are example means for automatically adjusting at least one hemodynamic parameter of the therapy signal generated by the IMD.

The various components and processing modules of the IMD may be housed in a common housing such as that shown in FIG. 6. Alternatively, portions of the IMD may be housed separately. For example, portions of therapy module 708 could be integrated with the IMD or provided in a separate housing. In this case, therapy module 708 may interact with therapy electrodes via an electrical cable, wireless link, or interface 724.

Figure 8:
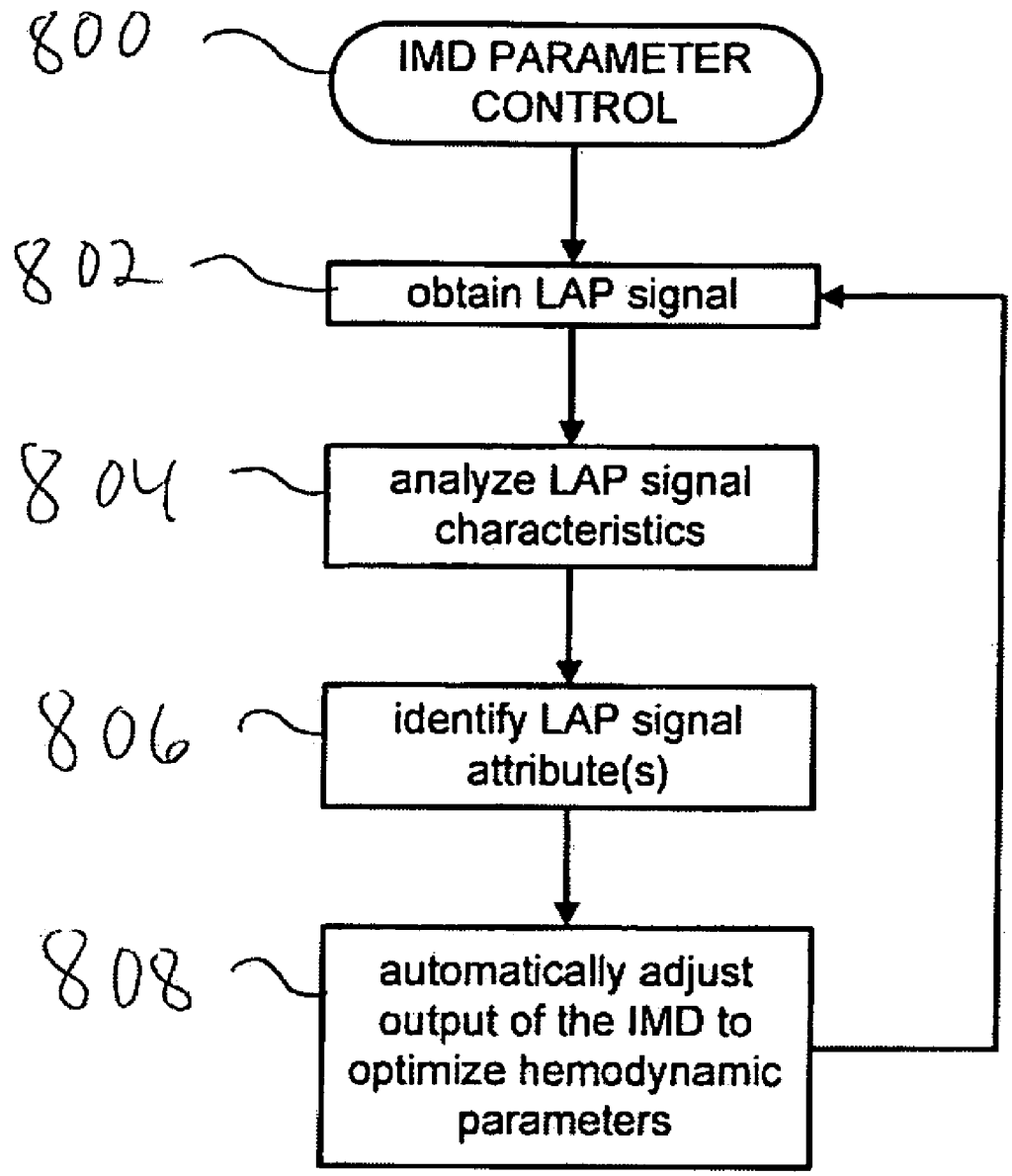
FIG. 8 is a flow diagram of an IMD parameter control process, which may be performed by an IMD configured in accordance with an example embodiment of the invention.

FIG. 8 is a flow diagram of an IMD parameter control process 800, which may be performed by an IMD configured in accordance with an example embodiment of the invention. The various tasks performed in connection with process 800 may be performed by software, hardware, firmware, or any combination thereof. For illustrative purposes, the following description of process 800 may refer to elements mentioned above in connection with FIGS. 1–7. In practical embodiments, portions of process 800 may be performed by different elements of the described system, e.g., data sources 712, processor architecture 700, or any component thereof. It should be appreciated that process 800 may include any number of additional or alternative tasks, the tasks shown in FIG. 8 need not be performed in the illustrated order, and process 800 may be incorporated into a more comprehensive procedure or process having additional functionality not described in detail herein.

IMD parameter control process 800 represents a generalized method for regulating and adjusting one or more operating parameters of an IMD such as a dual-chamber pacing device. In the preferred embodiment of the invention, process 800 represents a closed loop feedback control scheme performed by the IMD. Process 800 obtains a LAP signal (task 802) having the general characteristics and attributes described above in connection with FIG. 1 and FIG. 2. A number of LAP signal characteristics may be analyzed (task 804) to facilitate the identification of one or more LAP signal attributes (task 806). As mentioned above, these attributes may be associated with the LAP signal itself and/or associated with a signal derived from the LAP signal, such as the dLAP/dt signal. These attributes are indicative of cardiac performance and hemodynamic status of the patient. In a practical embodiment, the LAP signal attributes may include, without limitation: a temporal indicator based upon a-wave, v-wave, and/or c-wave characteristics, such as various time intervals; the amplitude of a-wave, v-wave, and/or c-wave peaks; the amplitude of x-wave, y-wave, and/or z-wave valleys; the slope of any a-wave, v-wave, and/or c-wave segment; the relative timing between local minima and/or local maxima of the dLAP/dt signal.

Generally, IMD parameter control process 800 processes the LAP signal characteristics and attributes and automatically adjusts a number of hemodynamic parameters of the IMD (task 808). In accordance with the example embodiment of the invention, task 808 is associated with the adjustment of the AV delay timing of a dual-chamber pacing device. Of course, task 808 may additionally (or alternatively) adjust other IMD parameters, including, without limitation: VV delay timing, which is the delay between pacing of both ventricles; AA delay timing, which is the delay between pacing of both atria; intra-atrium pacing delays for IMD's supporting multiple pacing leads in an atrium; intra-ventricle pacing delays for IMDs supporting multiple pacing leads in a ventricle; heart rate; lead location selection for IMDs supporting configurable activation of a plurality of leads in a single chamber (either the atrium and ventricle), which includes both therapy delivery and sensing leads. The IMD adjusts the hemodynamic parameter or parameters (or maintains its current operating status) in response to the identified LAP signal attribute or attributes. Of course, the specific adjustment mode, amount of adjustment, and frequency of adjustment will depend upon the current status of the patient, and the particular performance specifications of the IMD itself. As depicted in FIG. 8, process 800 preferably repeats itself, thus completing a continuous feedback control loop.

Figure 9:
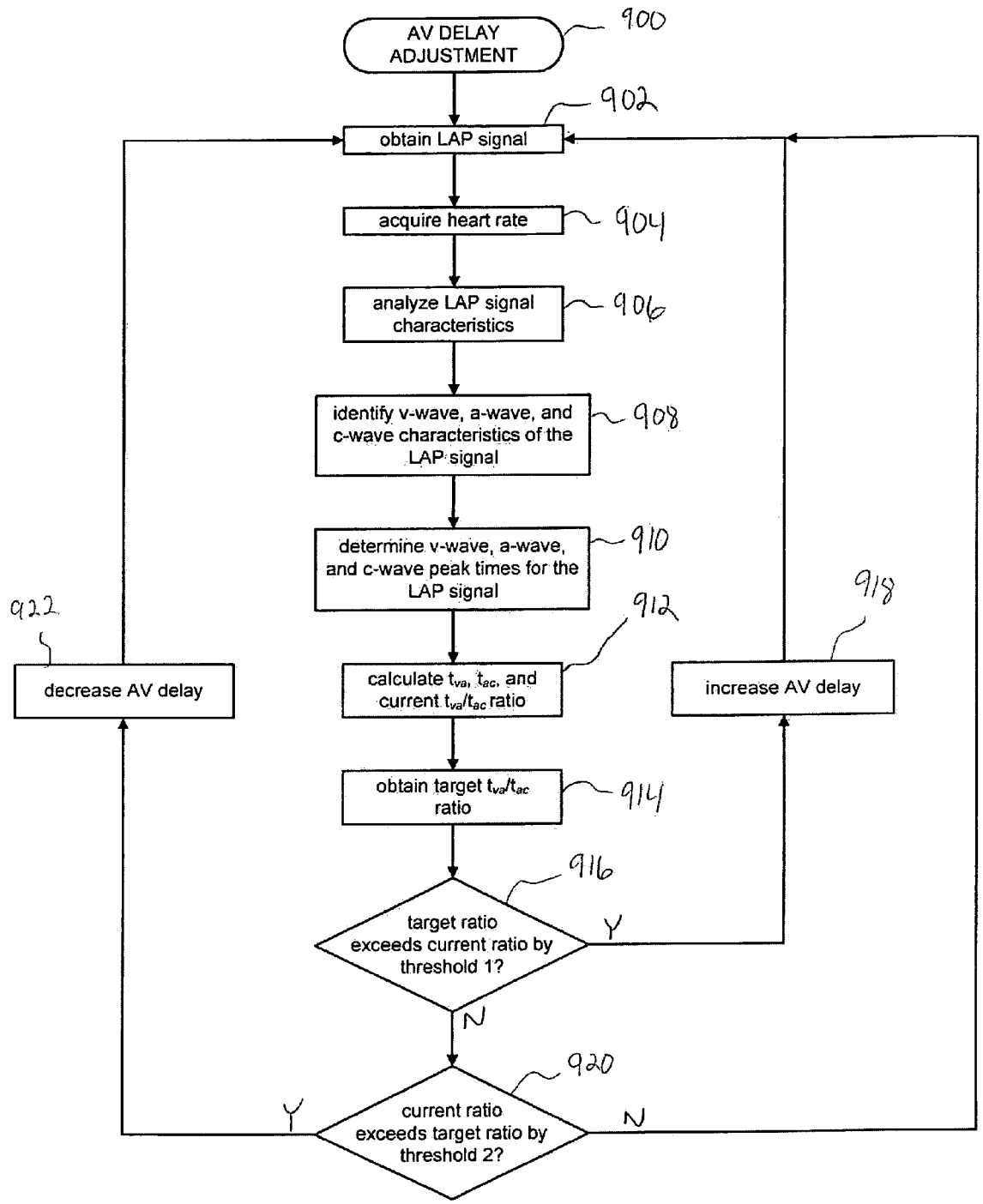
FIG. 9 is a flow diagram of an AV delay adjustment process, which may be performed by an IMD configured in accordance with an example embodiment of the invention.

FIG. 9 is a flow diagram of an AV delay adjustment process 900, which may be performed by an IMD configured in accordance with an example embodiment of the invention. The various tasks performed in connection with process 900 may be performed by software, hardware, firmware, or any combination thereof. For illustrative purposes, the following description of process 900 may refer to elements mentioned above in connection with FIGS. 1–7. In practical embodiments, portions of process 900 may be performed by different elements of the described system, e.g., data sources 712, processor architecture 700, or any component thereof. It should be appreciated that process 900 may include any number of additional or alternative tasks, the tasks shown in FIG. 9 need not be performed in the illustrated order, and process 900 may be incorporated into a more comprehensive procedure or process having additional functionality not described in detail herein.

AV delay adjustment process 900 obtains a LAP signal (task 902) having the general characteristics and attributes described above in connection with FIG. 1 and FIG. 2. In addition, process 900 may acquire the current heart rate of the patient (task 904) using any suitable technique. In the preferred practical embodiment, the heart rate acquired by process 900 is the real-time heart rate of the patient as measured by the IMD. Process 900 analyzes a number of LAP signal characteristics (task 906) to facilitate the identification of one or more LAP signal attributes. In particular, process 900 identifies the v-wave, a-wave, and/or c-wave characteristics of the LAP signal (task 908) using appropriate signal processing techniques. In this example, process 900 also determines the v-wave, a-wave, c-wave, and/or dLAP/dt peak times for each independent wave segment of the LAP signal (task 910).

AV delay adjustment process 900 may calculate various time periods and temporal relationships associated with the v-wave, a-wave, and/or c-wave peak times. For example, process 900 may calculate $t_{va}$, $t_{ac}$, and the current $$\frac{t_{va}}{t_{ac}}$$

ratio based upon the respective peak times (task 912). Furthermore, process 900 may obtain or compute a target $$\frac{t_{va}}{t_{ac}}$$

ratio, which represents a desired ratio for the current patient condition. In the example embodiment, the target ratio varies with the patient's heart rate and, therefore, task 914 may be associated with the adjustment of the target ratio in response to the heart rate acquired by task 904. The variable target ratio concept was described above in connection with FIG. 5.

The IMD can use the desired target ratio for comparison to the calculated ratio. For example, if the target ratio exceeds the current ratio by more than a first threshold value (query task 916), then AV delay adjustment process 900 increases the AV delay timing by a given incremental amount (task 918). If the target ratio does not exceed the current ratio by more than the first threshold value, then process 900 determines whether the current ratio exceeds the target ratio by more than a second threshold value (query task 920). If so, then process 900 decreases the AV delay timing by a given incremental amount (task 922). If not, then process 900 may maintain the current AV delay timing setting and simply repeat itself. In practical embodiments, the incremental amount of AV delay increase or decrease may be fixed or dynamic, and the amount of incremental increase or decrease may be selected to suit the needs of the particular IMD application. In addition, the threshold values (and whether two different thresholds are used) may be selected to suit the needs of the particular IMD application. Thresholds may be desirable to facilitate smooth and stable operation of the IMD and to minimize unnecessary adjustments that may otherwise be caused by noisy sensor signals or discontinuities in the sensor signals.

Figure 10:
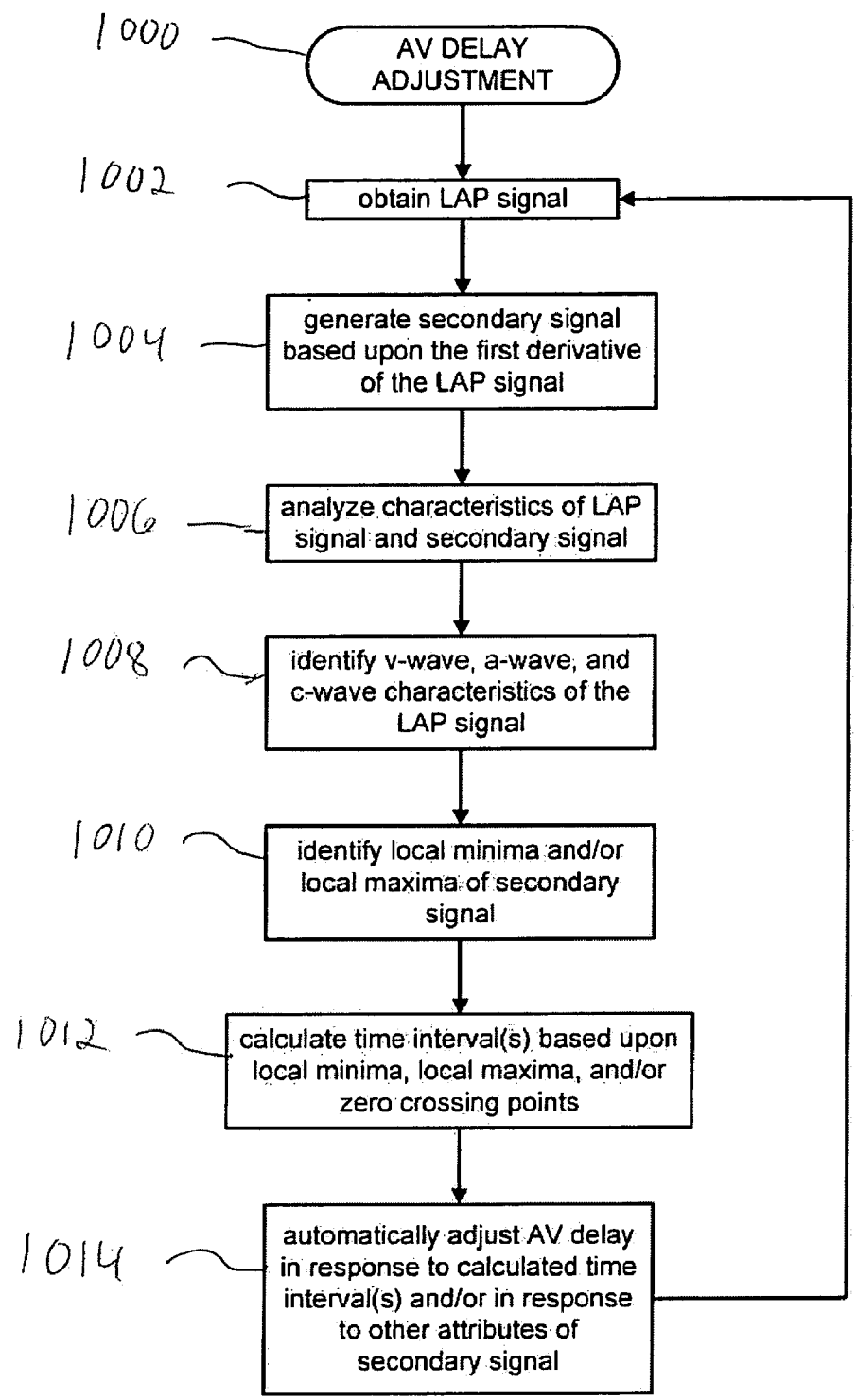
FIG. 10 is a flow diagram of an alternate AV delay adjustment process, which may be performed by an IMD configured in accordance with another example embodiment of the invention.

FIG. 10 is a flow diagram of an alternate AV delay adjustment process 1000, which may be performed by an IMD configured in accordance with another example embodiment of the invention. The various tasks performed in connection with process 1000 may be performed by software, hardware, firmware, or any combination thereof. For illustrative purposes, the following description of process 1000 may refer to elements mentioned above in connection with FIGS. 1–7. In practical embodiments, portions of process 1000 may be performed by different elements of the described system, e.g., data sources 712, processor architecture 700, or any component thereof. It should be appreciated that process 1000 may include any number of additional or alternative tasks, the tasks shown in FIG. 10 need not be performed in the illustrated order, and process 1000 may be incorporated into a more comprehensive procedure or process having additional functionality not described in detail herein.

AV delay adjustment process 1000 obtains a LAP signal (task 1002) having the general characteristics and attributes described above in connection with FIG. 1 and FIG. 2. The LAP signal is processed to generate a secondary signal that is based upon the first derivative of the LAP signal (task 1004). In accordance with one practical embodiment of the invention, task 1004 is associated with the generation of the dLAP/dt signal. Process 1000 analyzes a number of LAP signal characteristics and/or dLAP/dt signal characteristics (task 1006) to facilitate the identification of one or more LAP signal attributes. As mentioned above in connection with AV delay adjustment process 900, the IMD may identify the v-wave, a-wave, and c-wave characteristics of the LAP signal (task 1008), including the respective peak times. In addition, process 1000 may identify one or more signal attributes of the dLAP/dt signal. For example, process 1000 may identify local minima and/or local maxima of the dLAP/dt signal (task 1010). Referring to FIG. 1, local maximum 110 represents the maximum positive slope of the y-a segment of LAP signal 102, local maximum 112 represents the maximum positive slope of the z-c segment of LAP signal 102, and local minimum 114 represents the minimum negative slope of the c-x segment of LAP signal 102. Of course, process 1000 may identify other attributes or features of the dLAP/dt signal, including, without limitation: waveform morphology deviations or absence of applicable peaks or valleys of the applicable waveform segment; the relative maximum or minimum amplitude peaks associated with the a-z segment, c-x segment, x-v segment, -y segment, and y-a segment.

In addition to (or in lieu of) the LAP signal attributes, the attributes of the secondary signal (dLAP/dt) can be utilized to control the AV delay timing. For example, AV delay adjustment process 1000 may calculate one or more time intervals based upon the local maxima and/or local minima (task 1012). Moreover, the v-wave dLAP/dt zero crossing point to the z-wave dLAP/dt zero crossing point could be utilized to monitor left ventricular filling time. The separate timing intervals of left ventricular filling time can be determined by monitoring the v-wave dLAP/dt zero crossing point to the y-wave dLAP/dt zero crossing point representing the passive filling phase of the left ventricle and the y-wave dLAP/dt zero crossing point to the z-wave dLAP/dt zero crossing point representing the active filling phase of the left ventricle (atrial kick). The z-wave dLAP/dt zero crossing point to the c-wave dLAP/dt zero crossing point could be utilized to monitor left ventricular isovolumic contraction. The c-wave dLAP/dt zero crossing point to the x-v wave dLAP/dt maximum could be utilized to monitor the left ventricular ejection cycle. The x-v wave dLAP/dt maximum to the v-wave dLAP/dt zero crossing point could be utilized to monitor left ventricular isovolumic relaxation. The x-v wave dLAP/dt maximum to the z-wave dLAP/dt zero crossing point could be utilized to monitor left ventricular diastole. The z-wave dLAP/dt zero crossing point to the x-v wave dLAP/dt maximum could be utilized to monitor left ventricular systole.

Thereafter, process 1000 can automatically adjust the AV delay of the IMD in response to the calculated time interval(s) and/or in response to other attributes of the dLAP/dt signal (task 1014). For instance, process 1000 may adjust the AV delay in an attempt to maximize the slope of a specific segment of the LAP signal (i.e., increase a local maximum of the dLAP/dt signal or decrease a local minimum of the dLAP/dt signal). Generally, process 1000 can strive to optimize any attribute of the dLAP/dt signal that correlates to hemodynamic patient status and/or cardiac performance.

It should be appreciated that similar processes may be performed to adjust the AV delay (and/or other device parameters) in an attempt to optimize the amplitude of the c-wave peak, or to adjust IMD parameters based upon any LAP signal attribute or dLAP/dt signal attribute that correlates to hemodynamic performance. In addition, one or more of the optimization methodologies and algorithms described herein may be combined to provide an enhanced closed-loop adjustment technique. For example, a practical IMD may be suitably configured to adjust its parameters in a balanced attempt to reach a desired $$\frac{t_{va}}{t_{ac}}$$

ratio, a desired c-wave amplitude, and a desired slope for a given segment of the LAP signal.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

The invention claimed is:

1. A method for controlling implantable medical device parameters, said method comprising:
   obtaining a left atrial pressure signal;
   indentifying at least one attribute of said left atrial pressure signal, said at least one attribute being indicative of cardiac performance;
   automatically adjusting at least one output parameter of an implantable medical device to enhance hemodynamic performance in response to said at least one attribute, said left atrial pressure signal comprising a v-wave characteristic, an a-wave characteristic, and a c-wave characteristic;
   determining a v-wave peak time corresponding to said v-wave characteristic, an a-wave peak time corresponding to said a-wave characteristic, and a c-wave peak time corresponding to said c-wave characteristic; and
   calculating a first time period ($t_{va}$) based upon said v-wave peak time and said a-wave peak time, and a second time period ($t_{ac}$) based upon said a-wave peak time and said c-wave peak time, said at least one attribute corresponding to a ratio of $t_{va}$ and $t_{ac}$.

2. A method according to claim 1, wherein said ratio is $$\frac{t_{va}}{t_{ac}},$$

and said method calibrates said automatically adjusting step according to a target $$\frac{t_{va}}{t_{ac}}$$

ratio.

3. A method according to claim 2, further comprising:
   acquiring a measured heart rate; and
   altering said target $$\frac{t_{va}}{t_{ac}}$$

ratio in response to said measured heart rate.

4. A method for controlling implantable medical device parameters, said method comprising:
   obtaining a left atrial pressure signal;
   identifying at least one attribute of said left atrial pressure signal, said at least one attribute being indicative of cardiac performance; and
   automatically adjusting at least one output parameter of an implantable medical device to enhance hemodynamic performance in response to said at least one attribute, said left atrial pressure signal comprising a c-wave characteristic, and said at least one attribute comprising an amplitude of said c-wave characteristic.

5. A method according to claim 4, further comprising generating a secondary signal based upon a first derivative of said left atrial pressure signal, wherein said identifying step identifies at least one attribute of said secondary signal.

6. A method according to claim 4, said left atrial pressure signal comprising an a-wave characteristic and the c-wave characteristic, and said at least one attribute comprising a temporal indicator based upon said a-wave characteristic and said c-wave characteristic.

7. A method according to claim 4, wherein said automatically adjusting step adjusts an atrioventricular delay of said implantable medical device.

8. A method according to claim 4, further comprising repeating said obtaining, identifying, and automatically adjusting steps in a closed loop feedback control process.

9. A dual-chamber pacing implantable medical device comprising:
a data collection module configured to obtain a left atrial pressure signal from a patient;
a data processing module coupled to said data collection module, said data processing module being configured to identify at least one attribute of said left atrial pressure signal, and to correlate said at least one attribute to a hemodynamic status of said patient; and
a therapy module coupled to said data processing module, said therapy module being configured to automatically adjust at least one output parameter of a therapy signal in response to said at least one attribute, said left atrial pressure signal comprising a c-wave characteristic, and said at least one attribute comprising an amplitude of said c-wave characteristic.

10. A device according to claim 9, said data processing module being further configured to generate a secondary signal based upon a first derivative of said left atrial pressure signal, wherein said at least one attribute comprises at least one attribute of said secondary signal.

11. A device according to claim 9, said left atrial pressure signal comprising an a-wave characteristic and a c-wave characteristic, and said at least one attribute comprising a temporal indicator based upon said a-wave characteristic and said c-wave characteristic.

12. A device according to claim 9, wherein said output parameter comprises an atrioventricular delay of said therapy signal.

13. A dual-chamber pacing implantable medical device comprising:
a data collection module configured to obtain a left atrial pressure signal from a patient;
a data processing module coupled to said data collection module, said data processing module being configured to identify at least one attribute of said left atrial pressure signal, and to correlate said at least one attribute to a hemodynamic status of said patient; and
a therapy module coupled to said data processing module, said therapy module being configured to automatically adjust at least one output parameter of a therapy signal in response to said at least one attribute, said left atrial pressure signal comprising a v-wave characteristic, an a-wave characteristic, and a c-wave characteristic, said data processing module being further configured to:
determine a v-wave peak time corresponding to said v-wave characteristic, an a-wave peak time corresponding to said a-wave characteristic, and a c-wave peak time corresponding to said c-wave characteristic; and
calculate a first time period ($t_{va}$) based upon said v-wave peak time and said a-wave peak time, and a second time period ($t_{ac}$) based upon said a-wave peak time and said c-wave peak time, said at least one attribute corresponding to a ratio of $t_{va}$ and $t_{ac}$.

14. A dual-chamber pacing implantable medical device comprising:
means for obtaining a left atrial pressure signal of a patient;
means for identifying at least one attribute of said left atrial pressure signal, said at least one attribute being indicative of hemodynamic status of said patient;
means for automatically adjusting at least one output parameter of a therapy signal in response to said at least one attribute, said left atrial pressure signal comprising a v-wave characteristic, an a-wave characteristic, and a c-wave characteristic;
means for determining a v-wave peak time corresponding to said v-wave characteristic, an a-wave peak time corresponding to said a-wave characteristic, and a c-wave peak time corresponding to said c-wave characteristic; and
means for calculating a first time period ($t_{va}$) based upon said v-wave peak time and said a-wave peak time, and a second time period ($t_{ac}$) based upon said a-wave peak time and said c-wave peak time, said at least one attribute corresponding to a ratio of $t_{va}$ and $t_{ac}$.

15. A device according to claim 14, wherein said ratio is $$\frac{t_{va}}{t_{ac}},$$

and said means for automatically adjusting is configured to adjust said at least one output parameter according to a target $$\frac{t_{va}}{t_{ac}}$$

ratio.

16. A device according to claim 15, further comprising:
means for acquiring a measured heart rate of said patient; and
means for altering said target $$\frac{t_{va}}{t_{ac}}$$

ratio in response to said measured heart rate.

17. A device according to claim 14, further comprising means for calculating a timing interval based upon a derivative of said left atrial pressure signal, wherein said timing interval comprises at least one left atrial pressure signal attribute utilized to adjust a closed loop feedback control for hemodynamic optimization.

* * * * *